(12) United States Patent
Limousin

(10) Patent No.: US 6,937,898 B2
(45) Date of Patent: Aug. 30, 2005

(54) ACTIVE IMPLANTABLE MEDICAL DEVICE OF THE DEFIBRILLATOR/CARDIOVERTOR TYPE WITH SOPHISTICATED MANAGEMENT OF VENTRICULAR TACHYCARDIAS

(75) Inventor: Marcel Limousin, Paris (FR)

(73) Assignee: ELA Medical S.A., Montrouge (FR)

( * ) Notice: Subject to any disclaimer, the term of this patent is extended or adjusted under 35 U.S.C. 154(b) by 358 days.

(21) Appl. No.: 09/794,725

(22) Filed: Feb. 27, 2001

(65) Prior Publication Data

US 2001/0029392 A1 Oct. 11, 2001

(30) Foreign Application Priority Data

Feb. 29, 2000 (FR) .............................................. 00 02526

(51) Int. Cl.[7] .................................................. A61N 1/365
(52) U.S. Cl. ................................. 607/14; 607/9; 607/19
(58) Field of Search .............................. 607/17, 19, 4, 607/5, 9, 14

(56) References Cited

U.S. PATENT DOCUMENTS

| | | | | |
|---|---|---|---|---|
| 4,928,688 A | * | 5/1990 | Mower | 607/9 |
| 5,224,475 A | * | 7/1993 | Berg et al. | 607/8 |
| 5,995,870 A | | 11/1999 | Cazeau et al. | 607/9 |
| 5,999,850 A | | 12/1999 | Dawson et al. | 607/4 |
| 6,058,327 A | * | 5/2000 | Borgerding et al. | 607/9 |
| 6,185,459 B1 | * | 2/2001 | Mehra et al. | 607/14 |
| 6,324,425 B1 | * | 11/2001 | Blow et al. | 607/9 |
| 6,370,427 B1 | * | 4/2002 | Alt et al. | 607/4 |
| 6,421,564 B1 | * | 7/2002 | Yerich et al. | 607/9 |

FOREIGN PATENT DOCUMENTS

| | | | | |
|---|---|---|---|---|
| EP | 0 862 927 A1 | | 9/1998 | A61N/1/365 |
| WO | 98/40122 | | 9/1998 | A61N/1/39 |
| WO | 98/55178 | | 12/1998 | A61N/1/39 |

* cited by examiner

Primary Examiner—George R. Evanisko
(74) Attorney, Agent, or Firm—Orrick, Herrington & Sutcliffe LLP

(57) ABSTRACT

An active implantable medical device of the multisite defibrillator/cardioverter type having a sophisticated management of ventricular tachycardias. This device delivers a one of a defibrillation and/or cardioversion and/or ventricular antitachycardia pacing ("ATP") stimulation therapy mode, as desired and known in the art. The device senses the cardiac activity and detects in the sensed activity a disorder of the ventricular rhythm that is distinct from a ventricular fibrillation condition. The device also includes delivery of biventricular stimulation, connected to at least two ventricular sites, right and left, which is triggered on the detection of the aforesaid disorder of the ventricular rhythm prior to delivering the conventional ATP or shock therapy mode.

12 Claims, 1 Drawing Sheet

ACTIVE IMPLANTABLE MEDICAL DEVICE OF THE DEFIBRILLATOR/CARDIOVERTOR TYPE WITH SOPHISTICATED MANAGEMENT OF VENTRICULAR TACHYCARDIAS

FIELD OF THE INVENTION

The present invention is directed to "active implantable medical devices" as defined by the Jun. 20, 1990 directive 90/385/CEE of the European Communities Council, and more particularly to the family of the devices that deliver to the heart high energy pulses (i.e., pulses having an energy level notably exceeding the energy level provided during simple pacing stimulation) in order to try to terminate a tachyarrhythmia condition. These modes of therapy include a programmed high frequency stimulation mode referred to as "AntiTachycardia Pacing" ("ATP"), but with low level of stimulation energy pulses.

The devices having an ATP therapy mode are commonly known as "implantable defibrillators" or "implantable cardiovertors." It should be understood, however, that the invention also is directed to implantable defibrillator/cardiovertor/pacemaker, as well as implantable defibrillator/pacemaker devices.

BACKGROUND OF THE INVENTION

The aforementioned devices generally include a pulse generator which is able to monitor the patient's cardiac activity and to generate shock pulses of high energy when the heart presents a ventricular arrhythmia that is deemed suitable to be treated. When the pulse energy lies between 0.1 and approximately 10.0 Joules (J), this therapy is called "cardioversion" and the electric shock delivered is called "cardioversion shock." When the energy is higher than approximately 10.0 J, the therapy is called defibrillation and the electric shock is then called a "defibrillation shock."

Such devices are known in the art, as described, for example, in EP-A-0 626 182 and its corresponding U.S. Pat. No. 5,462,060, and EP-A-0 838 235 and its corresponding U.S. Pat. No. 5,868,793 (all commonly assigned to the assignee hereof Ela Medical S.A., Montrouge, France).

A tachyarrhythmia condition as used in this art and herein actually encompasses several different possible cardiac activity situations. These include ventricular fibrillation (VF), ventricular tachycardia (VT), sinusal tachycardia (ST), and supraventricular tachycardia (SVT, which is a tachycardia of atrial origin).

As soon as a disorder of the ventricular rhythm is recognized by the pulse generator and proven (i.e., is determined to be either ventricular tachycardia or ventricular fibrillation in the known manner), as known in the art, the currently available defibrillators generally apply a differentiated therapy, as follows. In the event of an organized ventricular tachycardia, there is first an application of an ATP therapy mode, which is then followed by application of a shock (cardioversion or defibrillation, as may be appropriate) if the ATP stimulation is ineffective. In the event of ventricular fibrillation, the therapy mode is an immediate application of a shock (again cardioversion or defibrillation, as appropriate in the case), which is the only appropriate therapy because the life of the patient is then deemed to be at risk.

In the first case (organized VT), except for some syncope episodes, the urgency of delivering a shock therapy mode is less than in the case of a VF, especially when the tachycardia is of a relatively low frequency. Certain clinical studies have suggested, however, that these two populations, one treated initially with ATP, the other immediately treated by a shock, present in fact during follow-up study an approximately identical number of delivered shocks. This would seem to suggest that the ATP therapy mode, even if it is effective, nevertheless does not prevent the occurrence of a more serious event requiring a treatment by a shock therapy mode.

One disadvantage of an immediate treatment with a shock is the pain felt by the patient, and the situation of discomfort in daily life in living in fear of a future shock.

It also has been suggested by certain studies that many VT conditions could terminate spontaneously, if it were possible to wait. Unfortunately, however, it is generally necessary to treat the patient quickly because these VT conditions are not well supported by the patent.

It is therefore desirable to provide a device that, in the event of an organized ventricular tachycardia, can apply at least temporarily a therapy mode other than a shock therapy, but which mode would be more effective than the known ATP stimulation therapy.

OBJECTS AND SUMMARY OF THE INVENTION

It is, therefore, an object of the present invention to provide an improvement of a medical device of the known type, e.g., a device according to the aforementioned EP-A-0 838 235 and U.S. Pat. No. 5,868,793, that is an implantable device including what are now known to persons of ordinary skill in the art as conventional means for delivering a defibrillation and/or cardioversion and/or ventricular anti-tachycardia stimulation therapy mode, means for sensing the cardiac activity, and means for detecting in the sensed activity a ventricular rhythm disorder distinct from a ventricular fibrillation.

According to the present invention, this device further comprises means for delivering a biventricular stimulation, connected to at least two ventricular sites, one right and one left, such that a biventricular stimulation is triggered in response to the detection of the aforesaid detected ventricular rhythm disorder.

According to an advantageous subsidiary characteristic of the invention, the means for sensing cardiac activity further operates to detect a ventricular rhythm and the means for detecting a ventricular rhythm disorder comprises (i) means for determining that the detected ventricular rhythm exceeds a threshold, (ii) means for detecting from said ventricular rhythm an episode of a ventricular tachycardia, or (iii) means for determining that the detected ventricular rhythm exceeds the threshold and detecting a ventricular tachycardia episode.

Another characteristic advantage of the invention concerns including in the device an activity sensor and means for re-synchronizing the stimulation of the left ventricle on a detected right ventricular activity (i.e., a spontaneous right ventricular contraction), the resynchronization means being triggered when the activity sensor indicates: (i) an absence of activity (i.e., the patient is determined to be at rest), and (ii) the ventricular rhythm is higher than a predetermined frequency threshold. The activity sensor may be of any type, preferably an accelerometer or minute ventilation type sensor, or a system that uses more than one such sensor, as such devices are well known in the art for, determining when a patient is in a rest condition or in an activity, i e., non-rest, condition.

In a preferred embodiment, when triggered, the means for delivering a biventricular stimulation operates with a reduction of the ventricular escape interval (relative to the ventricular escape interval normally applied otherwise).

In another alternate preferred embodiment, the means for detecting a ventricular rhythm disorder is preferably able, in the event of a persistent detection, to trigger the means for delivering the defibrillation and/or cardioversion and/or ventricular anti-tachycardia stimulation therapy mode, in particular after the passage of a predetermined time of continuous detection of the ventricular rhythm disorder. Persistence also may be determined when a ventricular rhythm disorder is detected in x out of y consecutive intervals.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which.

DETAILED DESCRIPTION OF THE INVENTION

One now will explain the present invention in more detail, with an example of one embodiment in which the invention can be implemented.

Figure 1:
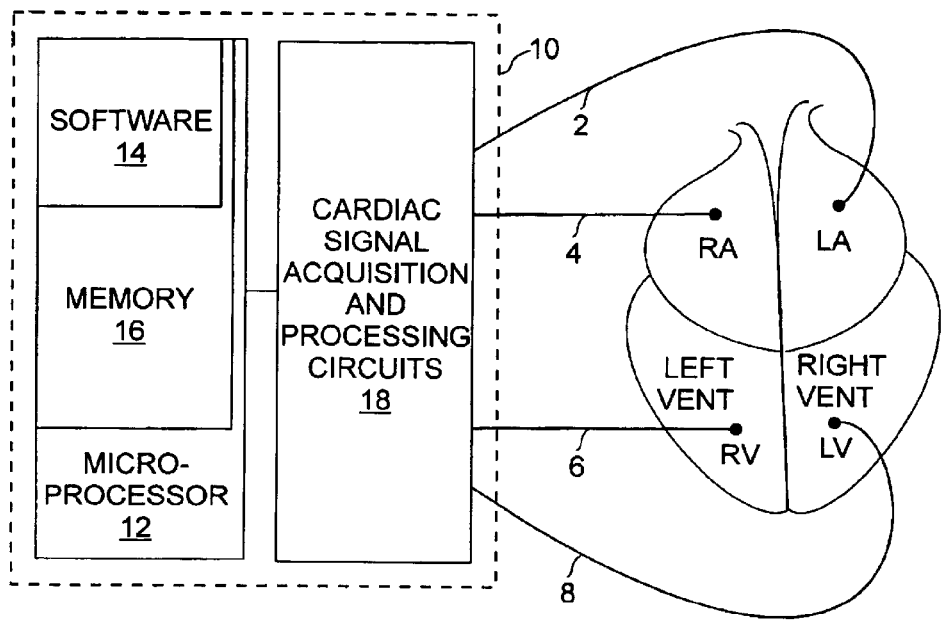
FIG. 1 is a schematic illustration of a device in accordance with the present invention.

The medical device of the invention, with reference to FIG. 1, is preferably a defibrillator or cardiovertor 10 of a type which is in itself well known, and of a type known as a "multisite" device. A multisite device is one in which electrodes 2, 4, 6 and 8 are placed in a plurality of distinct respective sites, with there being at least two ventricular sites, preferably one in the left ventricle LV and one in the right ventricle RV. The multisite device 10 can be any of the "double chamber" (double ventricular stimulation, LV, RV), "triple chamber" (right atrial stimulation RA and double ventricular, stimulation LV, RV) or even "quadruple chamber" (double atrial stimulation RA, LA, and double ventricular stimulation LV, RV) type devices.

In essence, the present invention proposes to improve the hemodynamic tolerance of certain tachycardias by a synchronous stimulation of the right and left ventricles, either by a mode triggered by a detection in one chamber, or by a light "overdriving" (stimulation of the two ventricles at a rate that is faster than the spontaneous rate). Moreover, the resynchronisation of the ventricles can, in certain circumstances, take part in the process of spontaneous arrest of the tachycardia, by interruption of a center of re-entry or by a rehomogenisation of the respective ventricular refractory periods.

Figure 2:
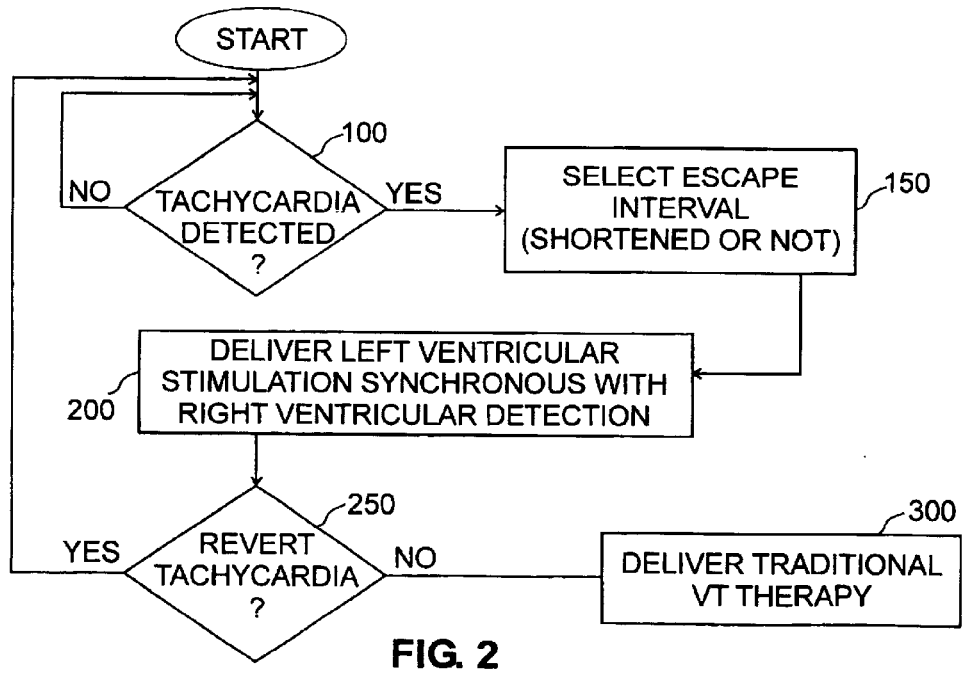
FIG. 2 is a flow chart in accordance with a preferred embodiment of the invention.

More particularly, according to the invention, and with reference to FIG. 2, the device will take an action either as soon as the ventricular rhythm reaches a threshold, for example, 120 bpm; or as soon as a ventricular tachycardia is detected (for example, in the manner described in the EP-A-0 626 182 and U.S. Pat. No. 5,462,060, and the EP-A-0 838 235 and U.S. Pat. No. 5,868,793 mentioned above); or, optionally, if one or more activity sensors indicate the absence of patient activity and if the ventricular rhythm remains higher than a threshold, e.g., 120 bpm. (stage 100). Then, on one of the foregoing events, the device will deliver a left ventricular stimulation, synchronous with the right ventricular detection (i.e., a resynchronisation) (stage 200).

Advantageously, one can envisage delivering a stimulation with a shortening of the ventricular escape interval relative to the ventricular escape interval associated with a simple stimulation (stage 150), while maintaining a biventricular stimulation in what is know as an "overdriving mode".

If the VT does not stop spontaneously within an acceptable delay following its detection, for example, after a programmable delay (for example, selected from between 10 to 10,000 ventricular cycles) (stage 250), the traditional therapy for attempting to stop the VT is then delivered by the device, namely either an ATP stimulation therapy mode or the application of a defibrillation or cardioversion shock therapy mode (stage 300). If an ATP stimulation is delivered, it can be delivered in either a monosite or a multisite mode, as desired by the practitioner. It should be understood, however, that the present invention is preferably implemented in software 14 resident in memory 16 of a microprocessor 12 controlled implantable device 10 using the existing cardiac signal acquisition and processing circuits and logic 18 although dedicated logic or solid state machines also could be used. The software 14 implements control functions performing the aforementioned analysis of the cardiac (ventricular rhythm) activity and control of the normal and biventricular stimulation and other modes of therapy delivered.

One skilled in the art will appreciate that the present invention can be practiced by other than the described embodiments, which are presented for the purposes of illustration and not of limitation.

I claim:

1. An active implantable medical device comprising:
   means for sensing a cardiac activity including a ventricular rhythm, and means for detecting in sensed activity a disorder of the ventricular rhythm that is distinct from a ventricular fibrillation;
   means for delivering a biventricular stimulation, connectable to at least two ventricular sites, a right and a left site, wherein said biventricular stimulation means is operated to deliver a biventricular stimulation therapy mode having low energy pulses in response to said detection of the ventricular rhythm disorder distinct from said ventricular fibrillation, for arresting said ventricular rhythm disorder;
   a threshold associated with a selected ventricular rhythm, wherein said means for sensing a cardiac activity further comprises means for detecting a right ventricular activity;
   an activity sensor having a first output responsive to an absence of patient activity; and
   means for resynchronizing the left ventricle stimulation to the detected right ventricular activity, said resynchronization means operating in response to the activity sensor output corresponding to an absence of patient activity and the detected ventricular rhythm being higher than said threshold.

2. The device of claim 1, further comprising a threshold associated with a selected ventricular rhythm, wherein the means for detecting a ventricular rhythm disorder further comprises means for detecting a ventricular rhythm and determining that the ventricular rhythm exceeds said threshold.

3. The device of claim 1, wherein the means for detecting a ventricular rhythm disorder further comprises means for detecting an episode of ventricular tachycardia.

4. The device of claim 1, wherein device further comprises a normal ventricular escape interval and the biventricular stimulation means, when triggered, operates with a second ventricular escape interval which is reduced relative to said normal ventricular escape interval.

5. The device of claim 1, further comprising means for delivering at least one of a defibrillation, a cardioversion, and a ventricular antitachycardia stimulation therapy mode, wherein the cardiac activity sensing means further comprises means for detecting a persistent detection of ventricular tachycardia activity, and wherein the means for detecting a ventricular rhythm disorder, in response to a persistent ventricular tachycardia detection, triggers the means for delivering at least one of said defibrillation, cardioversion, and ventricular antitachycardia stimulation therapy mode.

6. The device of claim 5, wherein the means for detecting said ventricular rhythm disorder further comprises means for determining that the detected ventricular rhythm disorder has continued for at least a predetermined time and in response thereto triggering the means for delivering the at least one of said defibrillation, cardioversion, and ventricular antitachycardia stimulation therapy mode to deliver said at least one therapy mode.

7. An active implantable medical device comprising:
means for sensing a cardiac activity including a ventricular rhythm and a right ventricular activity, and means for detecting in the sensed activity a disorder of the ventricular rhythm that is distinct from a ventricular fibrillation;
an activity sensor having a first output responsive to an absence of patient activity;
means for delivering a biventricular stimulation, connectable to at least two ventricular sites, a right and a left site, wherein said biventricular stimulation means is operated to deliver a biventricular stimulation therapy mode having low energy pulses in response to said detection of the ventricular rhythm disorder distinct from said ventricular fibrillation; and
means for resynchronzing the left ventricle stimulation to the detected right ventricular activity, said resynchronization means operating in response to the activity sensor output corresponding to an absence of patient activity and the detected ventricular rhythm being higher than a threshold.

8. The device of claim 7, further comprising the threshold associated with a selected ventricular rhythm, wherein the means for detecting a ventricular rhythm disorder further comprises means for detecting a ventricular rhythm and determining that the ventricular rhythm exceeds said threshold.

9. The device of claim 7, wherein the means for detecting a ventricular rhythm disorder further comprises means for detecting an episode of ventricular tachycardia.

10. The device of claim 7, wherein the device further comprises a normal ventricular escape interval and the biventricular stimulation means, when triggered, operates with a second ventricular escape interval which is reduced relative to said normal ventricular escape interval.

11. The device of claim 7, further comprising means for delivering at least one of a defibrillation, a cardioversion, and a ventricular antitachycardia stimulation therapy mode, wherein the cardiac activity sensing means further comprises means for detecting a persistent detection of ventricular tachycardia activity, and wherein the means for detecting a ventricular rhythm disorder, in response to a persistent ventricular tachycardia detection, triggers the means for delivering at least one of said defibrillation, cardioversion, and ventricular antitachycardia stimulation therapy mode.

12. The device of claim 11, wherein the means for detecting said ventricular rhythm disorder further comprises means for determining that the detected ventricular rhythm disorder has continued for at least a predetermined time and in response thereto triggering the means for delivering the at least one of said defibrillation, cardioversion, and ventricular antitachycardia stimulation therapy mode to deliver said at least one therapy mode.

* * * * *